US00PP23550P2

(12) United States Plant Patent
Kordes

(10) Patent No.: US PP23,550 P2
(45) Date of Patent: Apr. 23, 2013

(54) HYBRID TEA ROSE PLANT NAMED 'KORBATAM'

(50) Latin Name: *Rosa hybrida*
Varietal Denomination: KORbatam

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,215

(22) Filed: Jul. 25, 2011

(51) Int. Cl.
*A01H 5/00* (2006.01)

(52) U.S. Cl. ..... Plt./134

(58) Field of Classification Search ..... Plt./134
See application file for complete search history.

*Primary Examiner* — Kent L Bell

(57) ABSTRACT

A new and distinct variety of rose with long lasting, novel yellow flowers, and attractive foliage with excellent disease resistance. It exhibits moderate growth and an upright to bushy habit. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORbatam'.

The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORbatam'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The flower color of 'KORbatam' is yellow while the flower color of the seed parent is cream white.
2. The petal count of 'KORbatam' is double while the petal count of the seed parent is very double.

The new rose plant may be distinguished from its pollen parent, an 'un-named seedling' by the following combination of characteristics:

1. The flower color of 'KORbatam' is yellow while the flower color of the pollen parent is orange.
2. The disease resistance of 'KORbatam' is excellent while the disease resistance of the pollen parent is average.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORbatam' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbatam' was selected in May, 2002 from the seedling beds to be asexually propagated for further evaluation. The first asexual propagation of 'KORbatam' was done by budding to seedling understocks in July, 2002 at the inventor's nursery in Offenseth-Sparrieshoop, Germany.

This initial and other subsequent propagations conducted in controlled environments demonstrate that 'KORbatam' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KORbatam'.

DETAILED BOTANICAL DESCRIPTION

The following is a description of 'KORbatam', as observed growing in July, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORparofe', a rose variety from the same inventor described and illustrated in U.S. Plant Pat. No. 21,529 and issued on Nov. 30, 2010 are compared to 'KORbatam' in Chart 1.

CHART 1

| Characteristic | 'KORbatam' | 'KORparofe' |
|---|---|---|
| Average petal count: | 38-45. | 90-100. |
| Fragrance: | Moderate. | Strong. |
| Average number of buds per stem: | Singly. | Multiple, 5-6. |

Parents:

*Seed parent*.—An 'un-named seedling'.

*Pollen parent*.—An 'un-named seedling'.

Classification:

*Botanical classification*.—*Rosa hybrida* 'KORbatam'.

*Commercial classification*.—Hybrid Tea rose.

FLOWER AND FLOWER BUD

Blooming habit: Recurrent.

Flower bud:

*Size*.—Upon opening, 40 mm in length from base of receptacle to end of bud and 20 mm diameter at its widest point.

*Bud form*.—Long. Pointed ovoid.

*Bud color*.—As sepals first unfold, bud color is Yellow Group 13C. When ¼ open, the upper surface of petals is Yellow Group 6D, and the lower surface is Yellow Group 11C.

*Sepals*.—Color: Upper surface Green Group 146D. Lower surface Yellow-Green Group 146B. Intonations of Greyed-Red Group 182B on upper surfaces. Size: Average 35-40 mm (l)×5-10 mm (w). Shape: Triangular. Weak foliaceous appendages on two of the five sepals. Apex: Cirrose and apiculate. Base: Flat at union with receptacle. Quantity: Five. Surface texture: Upper side: Strong pubescence. Lower surface: Weak pubescence. Margins: Pubescent with occasional stipitate glands.

Receptacle:

*Surface*.—Smooth.

*Color*.—Yellow-Green Group 144A.

*Shape*.—Funnel-shaped.

*Size*.—10 mm (h)×8 mm (w).

Peduncle:

*Surface*.—Smooth.

*Length*.—70 to 80 mm average length.

*Diameter*.—2.5 to 3.0 mm average diameter.

*Color*.—Yellow-Green Group 144A.

*Strength*.—Strong.

*Borne*.—Singly.

*Anthocyanin*.—Greyed-Orange Group 175A.

Flower bloom:

*Fragrance*.—Moderate.

*Duration*.—On the plant 4 to 5 days. As a cut flower, 3 to 4 days. Senesced petals drop away cleanly.

*Size*.—Average for a hybrid tea rose. When open, the average flower diameter is 80-100 mm and the average flower height is 40 mm.

*Form*.—Shape of flower when viewed from the side: Upon opening, upper part: Flat. Upon opening, lower part: Flat. Open flower, upper part: Flattened convex. Open flower, lower part: Flattened convex.

Color:

*Upon opening, petals*.—Outermost petals: Outer Side: Yellow Group 9D. Inner Side: Yellow Group 11D. Innermost petals: Outer Side: Yellow Group 13C. Inner Side: Yellow Group 11A.

*Upon opening, basal petal spots*.—Basal petal spot, outermost petals: Outer Side: Yellow Group 8A. Inner Side: Yellow Group 8B. Basal petal spot, innermost petals: No distinctive coloration at petal base observed.

*After opening, petals*.—Outermost petals: Outer Side: Yellow-Orange Group 18D. Inner Side: Yellow-Orange Group 18D. Innermost petals: Outer Side: Yellow-Orange Group 18C. Inner Side: Yellow Group 13D and Yellow Group 12B in marginal zone.

*After opening, basal petal spots*.—Basal petal spot, outermost petals: Outer Side: Yellow Group 11A. Inner Side: Yellow Group 12A. Basal petal spot, innermost petals: Outer Side: Yellow Group 9B. Inner Side: Yellow Group 10A.

General tonality: On open flower Yellow-Orange Group 18A and 18B. No change in the general tonality at the end of the 3rd day. Afterwards, general tonality is Yellow Group 13D.

Petals:

*Petal count*.—Double to very double. Average Range: Approximately 38-45 petals under normal conditions.

*Petal reflex*.—Petals reflex somewhat.

*Petal edge*.—Entire.

*Petal shape*.—Obtuse. Apex shape is round. Shape of base is rounded.

*Petal size*.—On average 30-50 mm (l)×35-45 mm (w).

*Thickness*.—Average.

*Petal arrangement*.—Not formal.

Petaloids: Usually a few present.

*Petaloid count*.—Average of 2-6 per flower.

*Petaloid size*.—Petaloids are 10-20 mm long and 5-10 mm wide.

*Petaloid color*.—Color of inner side is Yellow Group 13C. Color of outer side is Yellow-Orange Group 16D.

*Petaloid texture*.—Smooth.

*Petaloid shape*.—Entire shape: Irregular. Ovate to subulate. Apex: Irregular obtuse to acute. Base: Obtuse to attenuate.

Reproductive organs:

*Pistils*.—Abundant. Approximately 35 present. Stigmas: Location: Slightly inferior in position to anthers. Color: Yellow-Orange Group 21D. Styles: Length: About 8-10 mm long. Color: Red Group 46C.

*Stamens*.—Approximately 50-60 on average and regularly arranged. Anthers: Size: About 2-3 mm long. Pollen: Generally present. Color: Yellow-Orange Group 22A. Filaments: Color: Yellow-Orange Group 14B. Length: About 9-11 mm.

THE PLANT

Growth: Moderate.

Plant habit: Upright to bushy habit. When grown as a budded field grown plant, the average plant height is 80-90 cm and the average plant width is 40 cm.

Stems:

*Stem color*.—Young wood: Yellow-Green Group 146C. Older wood: Yellow-Green Group 146B.

*Stem surface*.—Young wood: Smooth. Older wood: Smooth.

Prickles: Present.

*Incidence*.—Approximately 10 per each 10 cm of stem.

*Size*.—Average length: 9 mm.

*Color*.—Immature prickles: Greyed-Purple Group 183C. Mature prickles: Greyed-Orange Group 165C.

*Shape*.—Concave.

Leaves and leaflets: Normally 7 leaflets on normal leaves in middle of the stem.

*Venation pattern*.—Pyramidal net pattern.

*Leaf size*.—Approximately 140 mm (l)×70 mm (w).

*Abundance*.—Average.

*Texture*.—Leathery. Upper side of leaflet: Semi-glossy and smooth. Under side of leaflet: Matte and smooth.

*Color, mature foliage*.—Upper Leaf Surface: Green Group 137A. Lower Leaf Surface: Green Group 137C.

*Color, juvenile foliage*.—Upper Leaf Surface: Green Group 137A. Lower Leaf Surface: Green Group 137B.

*Anthocyanin intonation*.—Intonations present on juvenile leaflet margins, stipules, rachis, veins and margins. Color is Greyed-Purple Group 183B and 185B.

Stipules:

*Size*.—10 mm long. 8 mm between the tips of the stipules.

*Stipule color*.—Green Group 137C.

*Anthocyanin*.—Greyed-Purple Group 185B located on upper and lower surfaces.

*Margins*.—With numerous stipitate glands.

*Shape*.—Apex: Apiculate. Base: Slightly winged.

Petiole:

*Length*.—About 20 mm.

*Diameter*.—About 1 mm.

*Petiole color*.—Yellow-Green Group 144C.

*Underneath*.—Generally smooth with occasional stipitate glands and prickles.

*Margins*.—Light pubescence and stipitate glands.

*Anthocyanin*.—Greyed-Purple Group 183B on upper and lower surfaces.

Petiole rachis:

*Length*.—About 15 mm.

*Underneath*.—Generally smooth with occasional prickles.

*Diameter*.—About 1 mm.

*Color*.—Yellow-Green Group 144C.

*Margins*.—With fine pubescence and stipitate glands.

*Anthocyanin*.—Greyed-Purple Group 183B on upper and lower surfaces.

Leaflets:

*Size*.—Average size of the terminal leaflet is 55-65 mm (l)×35-45 mm (w).

*Shape*.—Entire leaflet: Ovate. Base: Obtuse. Apex: Acute.

*Margins*.—Finely serrated.

*Surface*.—Upper side: Semi-glossy and smooth. Underside: Matte and smooth.

*Texture*.—Leathery.

*Arrangement*.—Odd pinnate.

*Venation*.—Reticulate.

Hips/seed formation: None observed.

Winter hardiness: To date, the variety has been grown successfully in USDA Zones 6-9.

Disease resistance: Excellent resistance to powdery mildew (*Sphaerotheca pannosa*), rust (*Phragmidium* sp.), and blackspot (*Diplocarpon rosae*) diseases under normal growing conditions.

I claim:

1. A new and distinct variety of rose plant, as described and illustrated herein.

* * * * *

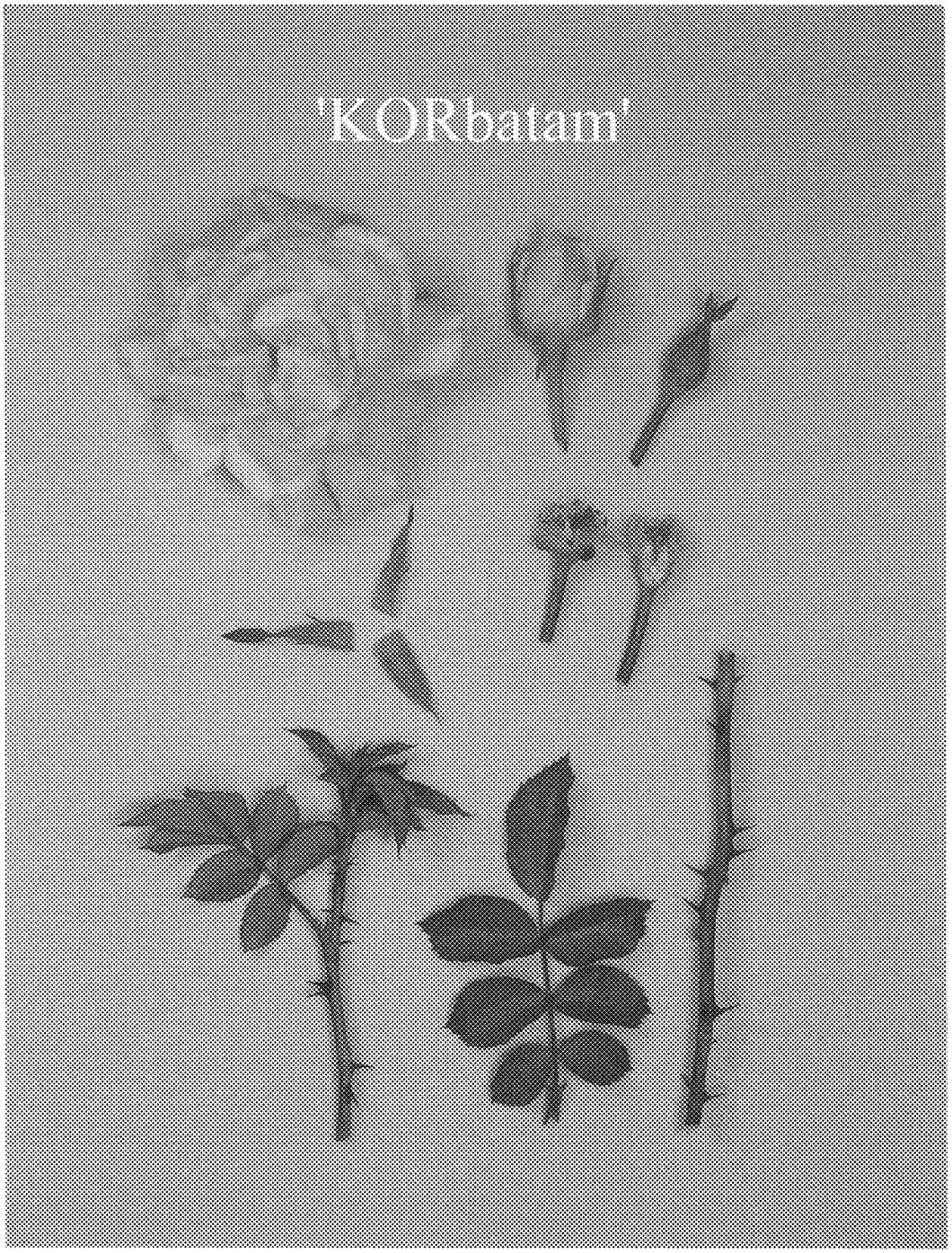
'KORbaiam'